United States Patent
Zhang

(10) Patent No.: US 9,993,833 B2
(45) Date of Patent: Jun. 12, 2018

(54) BLOCKED HOLE TREATMENT APPARATUS AND METHOD

(71) Applicant: BOE TECHNOLOGY GROUP CO., LTD., Beijing (CN)

(72) Inventor: Xindi Zhang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 103 days.

(21) Appl. No.: 15/073,189

(22) Filed: Mar. 17, 2016

(65) Prior Publication Data
US 2017/0028425 A1    Feb. 2, 2017

(30) Foreign Application Priority Data
Jul. 29, 2015 (CN) .......................... 2015 1 0456839

(51) Int. Cl.
| | |
|---|---|
| *B08B 3/00* | (2006.01) |
| *B05B 12/00* | (2018.01) |
| *G01N 29/24* | (2006.01) |
| *B05B 7/16* | (2006.01) |
| *G01N 29/02* | (2006.01) |

(52) U.S. Cl.
CPC .......... *B05B 12/004* (2013.01); *B05B 7/1686* (2013.01); *B05B 15/522* (2018.02); *G01N 29/022* (2013.01); *G01N 29/2437* (2013.01); *G01N 2291/0426* (2013.01)

(58) Field of Classification Search
None
See application file for complete search history.

(56) References Cited

U.S. PATENT DOCUMENTS

2015/0292079 A1   10/2015   Zou

FOREIGN PATENT DOCUMENTS

| CN | 101942641 A | 1/2011 |
| CN | 203238742 U | 10/2013 |
| CN | 103741096 A | 4/2014 |

OTHER PUBLICATIONS

EPO machine translation of CN103741096 (Zhou), retrieved from https://worldwide.espacenet.com/publicationDetails/biblio?CC=CN&NR=103741096A&KC=A&FT=D&ND=3&date=20140423&DB=&locale=en_EP on Nov. 26, 2017 (Year: 2017).*
Chinese Office Action in Chinese Application No. 201510456839.0, dated May 9, 2015 with English translation.
Second Chinese Office Action in Chinese Application No. 201510456839.0, dated Nov. 9, 2016 with English translation.

* cited by examiner

*Primary Examiner* — Eric W Golightly
(74) *Attorney, Agent, or Firm* — Collard & Roe, P.C.

(57) ABSTRACT

A blocked hole treatment apparatus and method are provided. The blocked hole treatment apparatus includes: a dredge element, a support element and a driving element, the dredge element is arranged on the support element, and the driving element is configured to drive the dredge element to rotate around the support element such that one end of the dredge element is inserted into a vent hole (the blocked hole) of the crucible.

18 Claims, 3 Drawing Sheets

BLOCKED HOLE TREATMENT APPARATUS AND METHOD

CROSS REFERENCE TO RELATED APPLICATIONS

Applicant claims priority under 35 U.S.C. § 119 of Chinese Application No. 201510456839.0 filed on Jul. 29, 2015, the disclosure of which is incorporated by reference.

TECHNICAL FIELD

Embodiments of the present disclosure relate to a blocked hole treatment apparatus and method.

BACKGROUND

Currently, an evaporation coater uses a crucible as the evaporation source such that the material can be evaporated directly from the crucible and leave from the gas outlet on the upper end of the crucible. However, during the burn of the material, it often happens that the gas outlet is blocked because of the condensation of the material at the gas outlet. This situation may typically be shown as follows. When confirming the presence of some material in the evaporation source, the evaporation rate thereof may be gradually reduced to zero while the temperature and power is increased continuously. After a while, the accumulated gas in the crucible may increase the internal pressure of the crucible and further burst through the material at the blocked hole. However, when the temperature approaches the alarm temperature before the cracking of the material, if the blocked hole has not been burst through by the material, there is no choice but to decrease the temperature and open the cavity, and then treat the blocked hole manually.

The blocked hole manual treatment method is summarized as: temperature decreasing—cavity opening—processing—vacuum pumping—temperature increasing. It can be seen that this set of procedures must be carried out under the circumstance that the cavity is open and the normal processing of the evaporation coating would be influenced. Furthermore, the whole treatment procedure consumes a long time of at least 4-6 hours, which would greatly influence the service efficiency of the device, and even would result in serious productivity loss. In this method, the blocked hole must be treated under the circumstance that the cavity is open such that the normal processing of the evaporation coating would be influenced, resulting in the problems of long time consuming and low efficiency.

SUMMARY

An embodiment of the present disclosure provides a blocked hole treatment apparatus, comprising: a dredge element, a support element and a driving element. The dredge element is arranged on the support element, and the driving element is configured to drive the dredge element to rotate around the support element such that an end of the dredge element is inserted into a vent hole (a blocked hole) of a crucible.

In some embodiments, the dredge element comprises a first connecting rod, a second connecting rod and a third connecting rod which are connected sequentially. The first connecting rod is connected with the driving element; the second connecting rod is rotatably connected with the support element, and the third connecting rod is configured to extend in a direction, for example, located above the crucible and extended towards the vent hole (blocked hole) of the crucible.

An embodiment of the present disclosure further provides a blocked hole treatment method for a crucible, comprising the following steps:

detecting the evaporation coating rate in the crucible by using a sensor; and sending the evaporation coating rate to a control element;

sending an action instruction from the control element to a driving element in a case where the evaporation coating rate is zero; and driving the dredge element to rotate around the support element by the driving element such that one end of the dredge element is pressed into a vent hole (the blocked hole) to dredge the vent hole (the blocked hole).

An embodiment of the present disclosure further provides a method for determining whether a material in a crucible is exhausted, comprising:

driving a dredge element to rotate around a support element by a driving element such that an end of the dredge element is pressed into a blocked hole or a vent hole to dredge the blocked hole or the vent hole; and then detecting an evaporation coating rate in the crucible; and sending the evaporation coating rate to a control element, wherein if the evaporation coating rate is zero, it is determined that the material in the crucible is exhausted; and if the evaporation coating rate is not zero, it is determined that the material in the crucible is not exhausted.

BRIEF DESCRIPTION OF THE DRAWINGS

In order to illustrate the technical solutions of the embodiments of the present disclosure more clearly, the figures of the embodiments are briefly described below. Apparently, the figures described below merely relate to some embodiments of the present disclosure rather than are limitative of the present disclosure.

Figure 1:
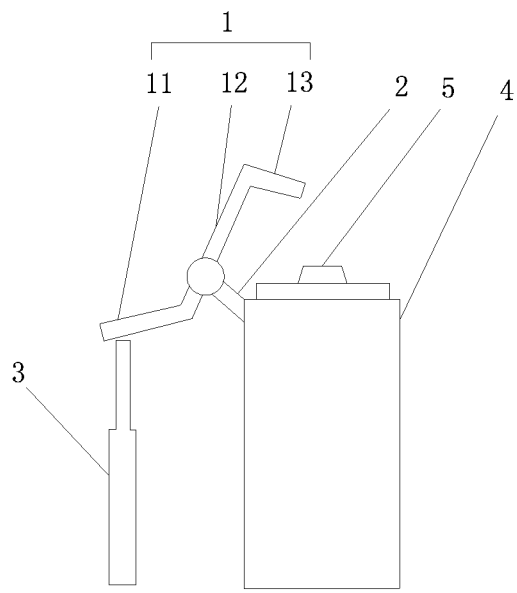
FIG. 1 is a schematic view of the initial state of a blocked hole treatment apparatus of an embodiment of the present disclosure.
Figure 2:
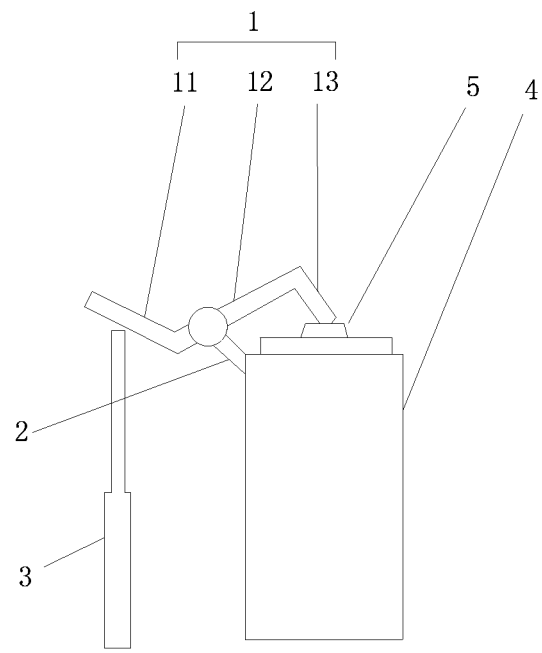
FIG. 2 is a schematic view of the operative state of a blocked hole treatment apparatus of an embodiment of the present disclosure.
Figure 3:
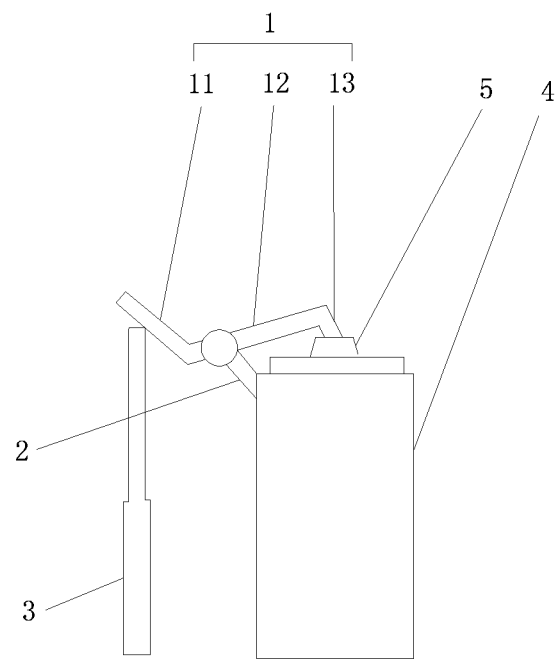
FIG. 3 is a schematic view of the dredging state of a blocked hole treatment apparatus of an embodiment of the present disclosure.
Figure 4:
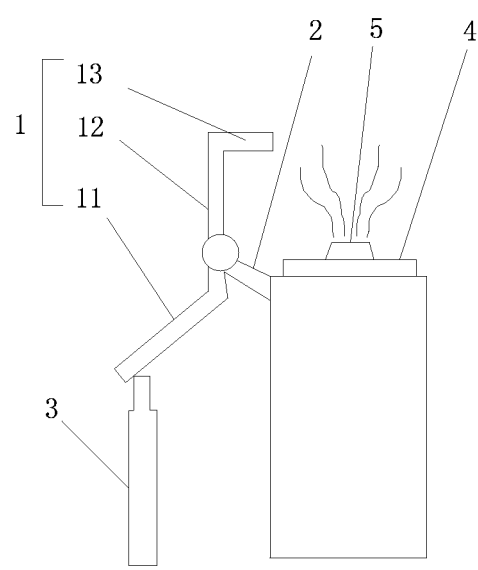
FIG. 4 is a schematic view of the finish state of a blocked hole treatment apparatus of an embodiment of the present disclosure.

Reference signs. 1: dredge element; 2: support element; 3: driving element; 4: crucible; 5: vent hole (blocked hole); 6: heating source; 7: heating wire; 11: first connecting rod; 12: second connecting rod; 13: third connecting rod.

DETAILED DESCRIPTION

To make the object, technical solutions, and advantages of the embodiments of the present disclosure clearer, the technical solutions of the embodiments of the present disclosure will be described below in a clearer and more complete way with reference to the figures of the embodiments of the present disclosure. Apparently, the embodiments described are only part, rather than all of the embodiments of the present disclosure. Based on the embodiments of the present disclosure described, all the other embodiments obtained by a person of ordinary skills in the art without paying inventive work fall into the scope of protection of the present disclosure.

In the description of the present disclosure, it needs to be noted that unless otherwise stated, "plurality" means two or more; the terms designating orientation or situation relationships, such as "above", "below", "left", "right", "inner", "outer", "front", "back", "head", "tail", etc., means the orientation or situation relationships shown in figures, which are used for convenience of describing the present disclosure briefly other than mean or hint that the apparatus or element must take the specific orientation or be configured and operated in the specific orientation, thereby the terms cannot be understood as the limitation for the present disclosure. Additionally, the terms "first", "second", "third" and others are used merely for the description purpose and cannot be understood as designating or meaning any relative importance.

In the description of the present disclosure, it needs to further noted that unless otherwise defined or limited, the terms "mounting", "connecting", "joining" should be understood in a broad sense. For example, it may be fixed connection or detachable connection or integral connection; it may be mechanical connection or electrical connection; or it may be direct connection or indirect connection via an intermedium. The specific meanings of the above terms in the present disclosure can be understood by those of ordinary skill in the art depending on the specific circumstances.

An embodiment of the present disclosure provides a blocked hole treatment apparatus, comprising: a dredge element, a support element and a driving element. The dredge element is arranged on the support element, and the driving element is configured to drive the dredge element to rotate around the support element such that an end of the dredge element is inserted into a vent hole (a blocked hole) of a crucible.

In some embodiments, the dredge element comprises a first connecting rod, a second connecting rod and a third connecting rod which are connected sequentially. The first connecting rod is connected with the driving element; the second connecting rod is rotatably connected with the support element, and the third connecting rod is configured to extend in a direction, for example, located above the crucible and extended towards the vent hole (blocked hole) of the crucible.

In some embodiments, the first connecting rod, the second connecting rod and the third connecting rod are connected sequentially to form a fold line.

In some embodiments, the first connecting rod, the second connecting rod and the third connecting rod are connected sequentially to form an S-shape.

In some embodiments, the support element comprises a support rod, one end of the support rod is rotatably connected with the dredge element and the other end of the support rod is fixed on the outer wall of the crucible on the other end.

In some embodiments, the one end of the support rod is rotatably connected with the dredge element through a rotation shaft.

In some embodiments, the one end of the support rod is rotatably connected with the dredge element through a hinge.

In some embodiments, the blocked hole treatment apparatus further comprises a control element and a sensor. The sensor is arranged inside of the crucible and configured to detect the evaporation coating rate and send the evaporation coating rate to the control element. The control element is electrically connected with the driving element.

In some embodiments, the driving element is a cylinder.

An embodiment of the present disclosure further provides a blocked hole treatment method for a crucible, comprising the following steps:

detecting the evaporation coating rate in the crucible by using a sensor; and sending the evaporation coating rate to a control element;

sending an action instruction from the control element to a driving element in a case where the evaporation coating rate is zero; and driving the dredge element to rotate around the support element by the driving element such that one end of the dredge element is pressed into a vent hole (the blocked hole) to dredge the vent hole (the blocked hole).

The above-mentioned technical solutions have the following beneficial effects. In the blocked hole treatment apparatus, the dredge element is driven to rotate around the support element by the driving element, thereby achieving the purpose of dredging the blocked hole automatically under the circumstance of not uncovering the cavity such that the process of normal evaporation coating would not be influenced. Moreover, the blocked hole treatment apparatus can be operated conveniently and the treatment consumes a short time and can efficiently improve the blocked hole treatment efficiency.

As shown in FIGS. 1-4, the blocked hole treatment apparatus provided in this embodiment comprises: a dredge element 1, a support element 2 and a driving element 3. The dredge element 1 is arranged on the support element 2, and the support element 2 acts as a pivot. Moreover, one end of the dredge element 1 is correspondingly arranged above a crucible 4 and the other end thereof is connected with the driving element 3. Meanwhile, the driving element 3 is configured to drive the dredge element 1 to rotate around the support element 2 such that one end of the dredge element 1 is inserted into the vent hole (blocked hole) 5 (the blocked hole means a vent hole being blocked by the material) of the crucible 4, thereby achieving the purpose of dredging the vent hole (blocked hole) 5 automatically under the circumstance of not uncovering the cavity such that the process of normal evaporation coating would not be influenced. Moreover, the blocked hole treatment apparatus can be operated conveniently and the treatment consumes a short time (the blocked hole treatment can be completed in as short as one minute) and can efficiently improve the blocked hole treatment efficiency.

Specifically, the dredge element 1 comprises a first connecting rod 11, a second connecting rod 12 and a third connecting rod 13 which are connected sequentially. The driving element 3 is located below the first connecting rod 11, connected on an end of the first connecting rod 11, and configured for driving the first connecting rod 11 to move up and down. The support element 2 is rotatably connected with the second connecting rod 12 which can be rotated around the connection point. The third connecting rod is arranged in correspondence with the vent hole (blocked hole) 5 of the crucible 4 and extended towards the vent hole (blocked hole) 5 of the crucible to ensure that the third connecting rod can be inserted into the vent hole (blocked hole) 5. That is, the first connecting rod 11 is jacked up by the driving element 3 to drive the second connecting rod 12 to rotate around the support element 2, which in turn drives the third connecting rod 13 to be pressed into the vent hole (blocked hole) 5 for the dredge treatment.

It needs to be noted that the form of the dredge element 1 is not limited as long as the dredge for the blocked hole 5 can be achieved according to the leverage theory. For example, the dredge element 1 may take the form of a fold line or an arc line.

When the dredge element 1 takes the form of a fold line, that is the first connecting rod 11, the second connecting rod 12 and the third connecting rod 13 are connected sequentially to form a fold line, the dredge is benefited. It can be produced by a crowbar structure which can be easily obtained.

Additionally, when the dredge element 1 takes the form of an arc line, the first connecting rod 11, the second connecting rod 12 and the third connecting rod 13 are connected sequentially to form an S-shape which is merely an approximate shape and not limited to any specific shape as long as an arc transition is used. Therefore, it may be called as a snake shape or a bird head shape.

Furthermore, the support element 2 comprises a support rod, one end of the support rod is rotatably connected with the dredge element 1 and the other end of the support rod is fixed on the outer wall of the crucible 4. The angle between the support rod and the outer wall of the crucible 4 can be adjusted flexibly. To facilitate to insert the dredge element into the vent hole (blocked hole) 5, the support rod can suitably inclined and arranged on the upper portion of the outer wall of the crucible 4.

Similarly, a rotatable element can be used to connect the support rod with the dredge element 1 according to actual requirements. For example, one end of the support rod is rotatably connected with the dredge element 1 through a rotation shaft. Specifically, a rotation shaft is arranged on one end of the support rod and passed through the second connecting rod 12 to enable the second connecting rod 12 to rotate along the circumferential direction of the rotation shaft.

Additionally, one end of the support rod may be rotatably connected with the dredge element 1 through a hinge. Specifically, a hinge is arranged on one end of the support rod and hinged with the second connecting rod 12. Therefore the rotation can be achieved similarly.

In this embodiment, the blocked hole treatment apparatus further comprises a control element and a sensor. The sensor is arranged inside of the crucible 4 and configured to detect the evaporation coating rate and send the evaporation coating rate to the control element. The control element is electrically connected with the driving element 3 for sending action instructions according to the evaporation coating rate. In some embodiments, the driving element 3 is a cylinder which is provided with an extendable rod for driving the first connecting rod 11 to move up and down.

The specific operating process is as shown in FIG. 1-4. When the extendable rod of the cylinder is extended out, the terminal end of the first connecting rod 11 is jacked, and then the front end of the third connecting rod 13 is pressed into the blocked hole 5 of the crucible 4 to stab the blocking material away. After that, the extendable rod of the cylinder is retracted, the front end of the third connecting rod 13 is raised and recovered such that the organic gas in the crucible 4 can be discharged normally.

Figure 5:
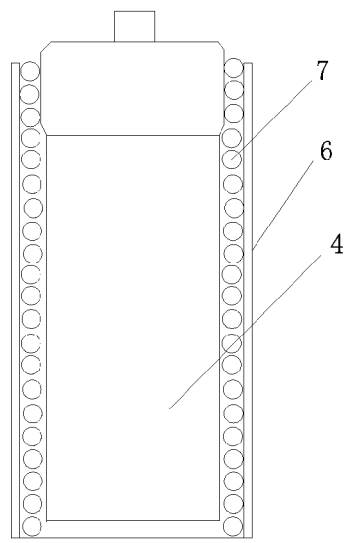
FIG. 5 is a structural schematic view of a crucible of an embodiment of the present disclosure.

The blocked hole treatment apparatus in this embodiment is mainly used in the OLED (Organic Light Emitting Diode) field. Correspondingly, as shown in FIG. 5, a heating source 6 and a heating wire 7 are arranged outside of the crucible 4. Meanwhile, the support element 2 is located outside of the heating source 6. Obviously, the blocked hole treatment apparatus may be suitable in other fields in which a hole of a crucible may be blocked.

Therefore, an embodiment of the present disclosure further provides a evaporation device, comprising a crucible having a vent hole and the above-mentioned blocked hole treatment apparatus.

Figure 6:
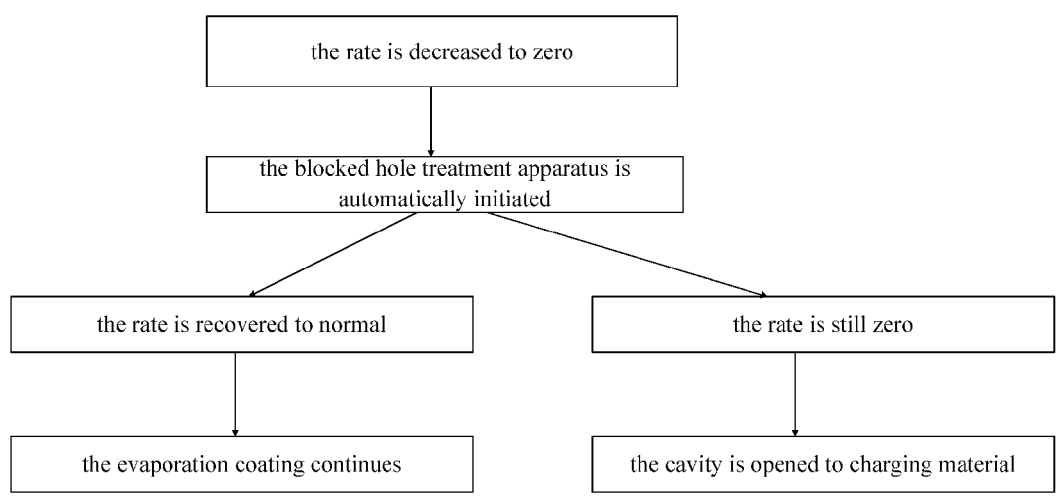
FIG. 6 is a block diagram of the principle of a blocked hole treatment method of an embodiment of the present disclosure.

Additionally, as shown in FIG. 6, the present disclosure further provides a blocked hole treatment method for a crucible, comprising the following steps:

S1. Detecting the evaporation coating rate in the crucible by using a sensor; and sending the evaporation coating rate to a control element. A crystal oscillator plate can be used as the sensor for detecting the rate because the rate is not zero during the normal evaporation coating of a normal crucible.

S2. Sending an action instruction from the control element to a driving element in a case where the evaporation coating rate is zero. An automatic control for the whole process can be achieved by using the control element and any manual intervention is not required.

S3. Driving the dredge element to rotate around the support element by the driving element such that one end of the dredge element is pressed into a vent hole (the blocked hole) of the crucible to dredge the vent hole.

Specifically, when the sensor detects a rate of zero, there are two situations, the material is exhausted or the hole is blocked. Whatever the reason of the rate of zero is, when the rate is zero, the driving element would be automatically initiated to dredge the vent hole (blocked hole) of the crucible.

Additionally, by using this method, it can be determined whether the material in the crucible is exhausted. If the hole is blocked, the rate after the dredge would be recovered to the normal level after the dredge is completed. If the material is exhausted, the rate after the dredge would be still zero in which case the cavity is required to be opened for charging material. Therefore, an embodiment of the present disclosure further provides a method for determining whether the material in a crucible is exhausted, comprising: driving a dredge element to rotate around a support element by a driving element such that one end of the dredge element is pressed into a blocked hole or a vent hole to dredge the blocked hole or the vent hole; and Then detecting the evaporation coating rate in the crucible immediately; and sending the evaporation coating rate to a control element. If the evaporation coating rate is zero, it is determined that the material in the crucible is exhausted. If the evaporation coating rate is not zero, it is determined that the material in the crucible is not exhausted.

In summary, the embodiment provides a blocked hole treatment apparatus, in which a dredge element is driven by a driving element to rotate around a support element, thereby achieving the purpose of dredging the blocked hole automatically under the circumstance of not uncovering the cavity such that the process of normal evaporation coating would not be influenced. Moreover, the blocked hole treatment apparatus can be operated conveniently and the treatment consumes a short time and can efficiently improve the blocked hole treatment efficiency.

The above description is merely exemplary embodiments which are not used for limiting the scope of protection of the present disclosure which is, however, determined by the attached claims.

The present application claims the priority of the Chinese Patent Application No. 201510456839.0 submitted on Jul.

29, 2015, and the content disclosed in the above Chinese patent application is incorporated herein by reference as part of this application.

What is claimed is:

1. A blocked hole treatment apparatus, comprising: a dredge element, a support element and a driving element, the dredge element being arranged on the support element, and the driving element being configured to drive the dredge element to rotate around the support element;
wherein the support element comprises a support rod, and one end of the support rod is rotatably connected with the dredge element.

2. The blocked hole treatment apparatus as defined according to claim 1, wherein the dredge element comprises a first connecting rod, a second connecting rod and a third connecting rod which are connected sequentially; the first connecting rod is connected with the driving element; the second connecting rod is rotatably connected with the support element; and the third connecting rod is configured to extend in a direction.

3. The blocked hole treatment apparatus as defined according to claim 2, wherein the first connecting rod, the second connecting rod and the third connecting rod are connected sequentially to form a polyline.

4. The blocked hole treatment apparatus as defined according to claim 2, wherein the first connecting rod, the second connecting rod and the third connecting rod are connected sequentially to form a S-shape.

5. The blocked hole treatment apparatus as defined according to claim 1, wherein the one end of the support rod is rotatably connected with the dredge element through a rotation shaft.

6. The blocked hole treatment apparatus as defined according to claim 1, wherein the one end of the support rod is rotatably connected with the dredge element through a hinge.

7. The blocked hole treatment apparatus as defined according to claim 1, further comprising a control element and a sensor, the sensor being configured to detect an evaporation coating rate and send the evaporation coating rate to the control element, and the control element being electrically connected with the driving element.

8. The blocked hole treatment apparatus as defined according to claim 7, wherein the driving element is a cylinder.

9. A blocked hole treatment method for a crucible, using the blocked hole treatment apparatus according to claim 1, comprising:
detecting an evaporation coating rate in the crucible by using a sensor; sending the evaporation coating rate to a control element;
sending an action instruction from the control element to the driving element in a case where the evaporation coating rate is zero; and
driving the dredge element to rotate around the support element by the driving element such that one end of the dredge element is pressed into a vent hole of the crucible to dredge the vent hole.

10. The method as defined according to claim 9, wherein the sensor is a crystal oscillator plate.

11. A method for determining whether a material in a crucible is exhausted, using the blocked hole treatment apparatus according to claim 1, the method comprising:
driving the dredge element to rotate around the support element by the driving element such that an end of the dredge element is pressed into a blocked hole or a vent hole to dredge the blocked hole or the vent hole; and
then detecting an evaporation coating rate in the crucible; and sending the evaporation coating rate to a control element, wherein if the evaporation coating rate is zero, it is determined that the material in the crucible is exhausted; and if the evaporation coating rate is not zero, it is determined that the material in the crucible is not exhausted.

12. A evaporation device comprising a crucible having a vent hole and the blocked hole treatment apparatus as defined according to claim 1.

13. The evaporation device as defined according to claim 12, wherein the dredge element comprises a first connecting rod, a second connecting rod and a third connecting rod which are connected sequentially; the first connecting rod is connected with the driving element; the second connecting rod is rotatably connected with the support element; and the third connecting rod is located above the crucible and extended towards the vent hole.

14. The evaporation device as defined according to claim 13, wherein the first connecting rod, the second connecting rod and the third connecting rod are connected sequentially to form a polyline.

15. The evaporation device as defined according to claim 12, wherein an other end of the support rod is fixed on an outer wall of the crucible.

16. The evaporation device as defined according to claim 15, wherein the one end of the support rod is rotatably connected with the dredge element through a rotation shaft.

17. The evaporation device as defined according to claim 16, wherein the one end of the support rod is rotatably connected with the dredge element through a hinge.

18. The evaporation device as defined according to claim 12, further comprising a control element and a sensor, the sensor being arranged inside of the crucible and configured to detect an evaporation coating rate and send the evaporation coating rate to the control element; and the control element being electrically connected with the driving element.

* * * * *